(12) United States Patent
Braun et al.

(10) Patent No.: US 6,525,213 B1
(45) Date of Patent: Feb. 25, 2003

(54) PROCESS FOR PREPARING ESTERS

(75) Inventors: Max Braun, Wedemark (DE); Kerstin Eichholz, Langenhagen (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 10/104,059

(22) Filed: Mar. 25, 2002

(30) Foreign Application Priority Data

Mar. 24, 2001 (DE) .......................................... 101 14 565

(51) Int. Cl.⁷ .............................................. C07C 69/76
(52) U.S. Cl. ........................ 560/51; 560/103; 560/174
(58) Field of Search ........................... 560/51, 103, 174

(56) References Cited

U.S. PATENT DOCUMENTS 5,405,991 A    4/1995   Feist et al.

FOREIGN PATENT DOCUMENTS

| DE | 19732031 | 4/1999 |
|---|---|---|
| DE | 10104663.4 | 2/2001 |
| EP | 463922 | * 1/1992 |

* cited by examiner

Primary Examiner—Paul J. Killos
(74) Attorney, Agent, or Firm—Crowell & Moring LLP

(57) ABSTRACT

An improved process for preparing carboxylic acid esters from acid chlorides, acid bromides or acids and alcohols provides for performing the esterification in the presence of the adduct (onium salt) of the corresponding carboxylic acid and 1,5-diazabicyclo[4.3.0]-non-2-ene or 1,8-diazabicyclo[5.4.0]-undec-7-ene. Alternatively, it is possible to operate in the presence of the corresponding carboxylic acid and an onium salt of the corresponding carboxylic acid.

16 Claims, No Drawings

PROCESS FOR PREPARING ESTERS

BACKGROUND OF THE INVENTION

The invention relates to a process for preparing carboxylic acid esters. Carboxylic acid esters can be used, for example, as solvents. They are also intermediates in chemical synthesis.

U.S. Pat. No. 5,405,991 discloses the preparation of esters of trifluoroacetic acid and of chlorodifluoroacetic acid from the acid chlorides and the corresponding alcohol in the presence of "onium" salts of the carboxylic acid corresponding to the carboxylic acid chloride used.

Published German patent application no. DE 197 32 031 discloses the preparation of esters of trifluoroacetic acid and of chlorodifluoroacetic acid in the presence of the corresponding "onium" salts with 2-phase formation for the purpose of simple separation of the products.

SUMMARY OF THE INVENTION

It is an object of the present invention to devise an improved process for the preparation of carboxylic acid esters from alcohols and carboxylic acids, carboxylic acid chlorides or carboxylic acid bromides.

These and other objects are achieved in accordance with the present invention by providing a process for preparing a carboxylic acid ester from an alcohol and a carboxylic acid, carboxylic acid chloride or carboxylic acid bromide, wherein esterification is effected while avoiding precipitation of "onium" salts, by operating in the presence of an onium salt adduct of the corresponding carboxylic acid and 1,5-diazabicyclo[4.3.0]-non-2-ene or 1,8-diazabicyclo[5.4.0]-undec-7-ene, or operating in the presence of the corresponding carboxylic acid and an onium salt of the corresponding carboxylic acid.

The process according to the invention for the preparation of carboxylic acid esters from alcohols and carboxylic acids, carboxylic acid chlorides or carboxylic acid bromides provides for the esterification to be performed, avoiding the precipitation of "onium" salts, by operating in the presence of the adduct ("onium" salt) of the corresponding carboxylic acid and 1,5-diazabicyclo[4.3.0]-non-5-ene ("DBN") or 1,8-diazabicyclo[5.4.0]-undec-7-ene ("DBU"), or operating in the presence of the corresponding carboxylic acid and an "onium" salt of the corresponding carboxylic acid.

Preferably the starting materials in the preparation of carboxylic acid esters according to the invention are alcohols and carboxylic acid chlorides. The advantage of the process of the invention is that the precipitation of solids (primarily hydrohalide salts of the "onium" cations) is prevented. Precipitated solids are undesirable in the reaction and working-up of the reaction mixture. The term "alcohols" also includes thioalcohols. The terms "carboxylic acids, carboxylic acid chlorides or carboxylic acid bromides" also cover the corresponding thiocarboxylic acids or thiocarboxylic acid derivatives.

The process will be explained in further detail with reference to illustrative representative embodiments using carboxylic acid chlorides. Preferably carboxylic acid esters corresponding to the formula (I) or (II)

  (I)

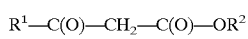  (II)

are prepared, wherein $R^1$ is C1–C4 alkyl or C1–C4 alkyl substituted by at least 1 halogen atom, and $R^2$ is C1–C4 alkyl, C1–C4 alkyl substituted by at least 1 halogen atom, aryl or benzyl. $R^1$ may also be aryl, e.g. phenyl. Particularly preferably, $R^1$ is methyl, ethyl or methyl or ethyl substituted by at least 1 halogen atom.

Particularly preferably, C1–C4-alcohols and acid chlorides of halogenated acetic acids or halogenated acetylacetic acids are esterified. Very particularly preferably, corresponding alkyl esters of chloro-, dichloro-, trichloro-, trifluoro-, difluoro- or chlorodifluoroacetic acid are prepared, or corresponding alkyl esters of tri-, difluoro- or chlorodifluoroacetylacetic acid, in particular of trifluoroacetylacetic acid.

The invention can be performed in two variants. In the first variant, the "onium" salts of two special amines, DBN or DBU, are used. In this case, no additional acid is used. In the second variant, the reaction is performed in the presence of free carboxylic acid. In this variant, any nitrogen-based "onium" salts can be used, including DBN and DBU. The second variant will be explained in greater detail first.

According to one variant, the esterification is performed in the presence of an "onium" salt of the corresponding acid (preferably of a halogenated acetic acid or of the halogenated acetylacetic acid) and additionally of the corresponding (free) acid (preferably of a halogenated acetic acid or of (free) halogenated acetylacetic acid). Accordingly, both a corresponding "onium" salt and the free acid are present in the mixture. It is assumed that a portion of the corresponding halogenated acid can be replaced by another carboxylic acid or mineral acid. However, it is preferred if the acid chloride and the acid used to form the "onium" salt are the same. The molar ratio of "onium" salt to (free) carboxylic acid is advantageously between 1:0.2 and 1:3. Good results are for example also achieved with a ratio between 1:0.2 and 1:2. The concentration of "onium" salt is advantageously 5 to 20 mole % of the reactants (calculated without solvent). The presence of the free carboxylic acid can be brought about by adding it to the reaction mixture. It can also be produced in situ by adding water to the reaction mixture, because the acid chloride and water react to form the corresponding free carboxylic acid. The process can be performed continuously.

The term "onium" in this variant indicates cations having a positively-charged nitrogen, for example protonated aromatic nitrogen bases such as pyridinium or protonated alkyl-, dialkyl- or trialkylammonium cations, or ammonium compounds substituted by cycloalkyl, or cycloaliphatic nitrogen bases such as piperidinium or quaternary ammonium cations.

Especially suitable carboxylic acid salts are "Onium" salts in which "onium" identifies a cation of nitrogen having the formula R'R"R'''R''''N+ wherein R', R", R''' and R'''', independently of each other, represent hydrogen, alkyl with 1 to 20 carbon atoms, aryl or aralkyl. R' and R" or R''' and R'''', or R', R' and R''' or R', R", R''' and R'''' may also, optionally with inclusion of the nitrogen atom, form saturated or unsaturated ring systems. "Aryl" here stands in particular for phenyl or for phenyl substituted by 1 or more C1–C2 alkyl groups. Particularly advantageous salts are those in which "onium" is ammonium, pyridinium or $R^{1'}R^{2'}R^{3'}R^{4'}N^+$, wherein $R^{1'}$, $R^{2'}$, $R^{3'}$ and $R^{4'}$, independently of each other, represent hydrogen, alkyl with 1 to 15 carbon atoms, phenyl or benzyl. Examples of such cations include pyridinium, piperidinium, N-methylpiperidinium, anilinium, benzyltriethylammonium and triethylammonium.

Amines substituted by hydroxy groups, particularly cycloaliphatic amines, in particular hydroxy-substituted piperidines and N- C1–C4 alkylpiperidines, can also be used.

Suitable examples include piperidines substituted at the C4 atom such as 4-hydroxypiperidine, N-methyl-4-hydroxypiperidine, N-ethyl-4-hydroxypiperidine and N-propyl-4-hydroxypiperidine.

Cations of amines which are disclosed in German Offenlegungsschrift no. DE 101 04 663.4, which does not constitute a prior publication, can also be used. These are "onium" cations based on a mono-or bicyclic compound with at least two nitrogen atoms, wherein at least one nitrogen atom is incorporated in the ring system. Thus "onium" cations based on monocyclic compounds may be used. These are then saturated or unsaturated 5-member ring, 6-member ring or 7-member ring compounds. At least one nitrogen atom is incorporated in the ring. A further nitrogen atom may also be incorporated in the ring system. Alternatively or additionally, the ring may be substituted by one or more amino groups. Dialkylamino groups in which the alkyl groups may be identical or different and comprise 1 to 4 carbon atoms are preferred. The amino group may also represent a saturated ring system, for example a piperidino group. Representatives of monocyclic ring systems which can be used effectively include dialkylaminopyridine, dialkylaminopiperidine and dialkylaminopiperazine.

"Onium" cations of bicyclic compounds may also be used. Here too, one, two or more nitrogen atoms may be integrated in the ring system. The compounds may be substituted by one or more amino groups. Dialkylamino groups in which the alkyl groups may be identical or different and comprise 1 to 4 carbon atoms or together with the nitrogen atom form a saturated ring system, such as for example the piperidinyl group, are again preferred.

It should be apparent from the foregoing that in this embodiment at least two nitrogen atoms in the usable compounds must have basic properties and, depending on the type of bonds, are bonded to 2 or 3 carbon atoms.

"Onium" salts of carboxylic acid with bicyclic amidines, in particular 1,5-diazabicyclo[4.3.0]-non-2-ene (DBN) and 1,8-diazabicyclo[5.4.0]-undec-7-ene (DBU) are very particularly preferred. These salts can also be used together with free carboxylic acid, as is possible with the "onium" salts described generally above.

Another variant of the invention provides for operation to be in the presence of the adduct ("onium" salt) of the corresponding carboxylic acid and 1,5-diazabicyclo-[4.3.0]-non-2-ene or 1,8-diazabicyclo-[5.4.0]-undec-7-ene. In this variant, the process is carried out without the presence of additional free acid.

The above "onium" compounds can be prepared in advance, by reacting the amines with the respective acid.

The temperature at which the reaction is carried out in the process of the invention may range from ambient temperature (approximately 20° C.) up to the boiling point of the mixture, for example up to 100° C. The process may be carried out at ambient pressure (approximately 1 bar absolute) or if desired also at elevated pressure, for example at a pressure of up to 5 bar absolute.

The process may be carried out either batchwise or continuously. The resulting reaction mixture may be worked-up by, for example, distillation in order to recover the product esters.

In one preferred embodiment, the formation of two phases is utilized to recover the product. This may be effected, for example, by cooling the reaction mixture to low temperatures. One phase is represented by the ester phase, which often is already highly pure.

With other esters, phase separation already occurs at ambient temperature. This applies, for example, to the methyl and ethyl esters of trifluoroacetic acid or chlorodifluoroacetic acid disclosed in co-pending U.S. patent application Ser. No. 09/113,547, filed Jul. 10, 1998 (=DE 197 32 031). Advantageously, a molar ratio of alcohol to acid chloride, as described in the aforementioned German patent specification, is set in the range of 1.01:1 to 5:1. Preferably the molar ratio of methanol to trifluoroacetyl chloride is about 1.03:1 to 4:1, the molar ratio of ethanol to trifluoroacetyl chloride is about 1.01:1 to 5:1, the molar ratio of methanol to chlorodifluoroacetyl chloride is about 1.06:1 to 2.5:1 and the molar ratio of ethanol to chlorodifluoroacetyl chloride is about 1.02:1 to 2.5:1.

In the ester production process of the invention, HCl is released when using acid chlorides. The released HCl can react with alcohol to form an alkyl chloride. It has been found that alkyl chloride formation can be largely suppressed if non-aromatic "onium" salts are used, in particular trialkylammonium compounds. Advantageously the suppression of alkyl chloride formation is also successful, in particular with a continuous process and removal of a two-phase mixture from the bottom of the reactor, by feeding back the catalyst phase which has been separated (which contains "onium" carboxylic acid salt) into those components of the reactor in which alcohol and HCl are in contact with each other, for example in the stripper or those components in which evaporating constituents of the reaction mixture are condensed under reflux.

The invention also relates to novel "onium" salts which can be used as a catalyst in the esterification process according to the invention. These are salts which are formed of carboxylic acid anions and "onium" cations based on a mono- or bicyclic compound with at least two nitrogen atoms, in which at least one nitrogen atom is incorporated in the ring system. The preferred carboxylic acid anions are those which correspond to the aforedescribed carboxylic acid esters of formula (I) or (II). Particularly preferred are carboxylic acid anions which correspond to the carboxylic acid esters described further above as being preferred. Usable and preferred "onium" cations are listed above. Particularly preferred are "onium" salts formed from dialkylaminopyridinium, dialkylaminopiperidinium or dialkylaminopiperazinium cations, the aforementioned hydroxysubstituted piperidinium cations or protonated cations of DBN and DBU as cations and trifluoroacetate, difluoroacetate, chlorodifluoroacetate, trifluoroacetylacetate, chlorodifluoroacetylacetate and difluoroacetylacetate. Salts formed from protonated cations of DBN and DBU and trifluoroacetate are very particularly preferred. The aforementioned salts may be used as a catalyst in the process of the invention.

The invention additionally relates to mixtures which comprise carboxylic acids and nitrogen-based salts of "onium" cations and carboxylic acid anions corresponding to the carboxylic acid in the mixture. The molar ratio of "onium" salt to carboxylic acid lies in the range from 1:0.2 to 1:3. Preferred "onium" cations (be it with one or with at least two nitrogen atoms) are described above. Preferred carboxylic acid anions are likewise described above. The mixtures according to the invention of "onium" salts and carboxylic acid are likewise usable as catalysts in the esterification process according to the invention. The advantage of the process according to the invention is better handling, since the precipitation of solids is avoided, and the possibility of decreasing the formation of by-products, in particular reduced alkyl chloride formation when using carboxylic acid chlorides in the esterification.

The following examples are intended to illustrate the invention in further detail, without limiting its scope.

Preparation of Ethyl Chloride-free Ethyl Trifluoroacetate

EXAMPLE 1

Use of Onium Acetate, Trifluoroacetic Acid and Water

| Batch: | | |
|---|---|---|
| | 1.0 mole ethanol | 32.05 g |
| | 0.1 mole trifluoroacetic acid | 11.40 g |
| | 0.1 mole triethylamine | 10.10 g |
| | 1.0 mole trifluoroacetyl chloride (TFAC) | 132.47 g |
| | 0.025 mole water | 0.45 g |

Set-up and Procedure:

The alcohol was introduced into a 250 ml three-necked flask, and the amine was weighed in. Then the trifluoroacetic acid was added dropwise very carefully. Then the water was also added, in order to produce a two-phase system. The flask was provided with a reflux condenser (−40° C.) and heated to approximately 55° C. in an oil bath. At this temperature, TFAC was introduced with stirring. When between 27 and 30 g TFAC (~20 mole %) had been added, the solution became cloudy and formed a second phase (the upper phase contained the catalyst). Sample 01 was taken from the liquid ester phase, and Sample 02 from the gas phase above the reaction mixture. When 70.1 g TFAC had been added, the upper phase was only approximately 2 mm thick. Sample 03 was taken therefrom (ester phase). With 80 g ~60 mole %, then only one phase was still present.
Result (analysis in each case in % GC surface area):

| Sample | % HCl | % TFAC | % EtCl | % EtOH | % TFAEt |
|---|---|---|---|---|---|
| 01 | 1.22 | 0.31 | | 5.70 | 92.32 |
| 02 | 48.61 | | 0.69 | 0.17 | 50.08 |
| 03 | 3.97 | 0.77 | | 1.23 | 87.31 |

Ethyl chloride could be detected only in the gas phase.

EXAMPLE 2

Use of DBN

| Batch: | 1.0 mole ethanol | 32.05 g |
|---|---|---|
| | 0.1 mole trifluoroacetic acid (TFA) | 11.40 g |
| | 0.1 mole 1,5-diazabicyclo[4.3.0]-non-2-ene (DBN) | 12.40 g |
| | 1.0 mole trifluoroacetyl chloride (TFAC) | 132.47 g |

Set-up and Procedure:

The alcohol was introduced into a 250 ml three-necked flask, and the amine was weighed in. Then the trifluoroacetic acid (TFA) was added dropwise very carefully. DBN reacted very much more vigorously with the TFA than e.g. pyridine. The flask was provided with a reflux condenser (−40° C.) and heated to approximately 55° C. in an oil bath. At this temperature, TFAC was introduced with stirring. When approximately 33 g TFAC (~20 mole % relative to the quantity of ethanol used) had been added, the solution became cloudy, and after addition of 40 g, a clear, second phase formed (the upper phase was the ester phase). Sample 01 was taken from the liquid ester phase, and Sample 02 from the gas phase above reaction mixture. When 88 g (~68 mole %) had been added, only one phase was still present.

Result:

| Sample | % HCl | % TFAC | % EtCl | % EtOH | % TFAEt |
|---|---|---|---|---|---|
| 01 | 1.70 | 1.31 | | | 96.19 |
| 02 | 62.67 | 0.72 | 0.15 | 0.09 | 29.32 |
| 03 | | 0.77 | 0.03 | 0.04 | 98.99 |

Sample 03 was taken only after the introduction of the complete quantity of TFAC and was worked up by hydrolysis.

EXAMPLE 3

Use of 4-Hydroxy-N-Methylpiperidine

| Batch: | 1.0 mole ethanol | 32.05 g |
|---|---|---|
| | 0.1 mole trifluoroacetic acid | 11.40 g |
| | 0.1 mole 4-hydroxy-N-methylpiperidine | 11.50 g |
| | 1.0 mole trifluoroacetyl chloride (TFAC) | 132.47 g |
| | 0.093 mole water | 1.68 g |

Set-up and Procedure:

The alcohol was introduced into a 250 ml three-necked flask, and the amine was weighed in. Then the trifluoroacetic acid was added dropwise very carefully. Then the water was also added, in order to produce a two-phase system. 4-hydroxy-N-methylpiperidine did not react so vigorously with the TFA as e.g. DBN. The flask was provided with a reflux condenser (−40° C.) and heated to approximately 55° C. in an oil bath. At this temperature, TFAC was introduced with stirring. When approximately 40 g TFAC (~30 mole %) had been added, the solution became cloudy, and formed a clear, second phase (the "onium" salt formed the upper phase). Sample 01 was then taken. After 78 g TFAC (~60 mole %) had been added, two phases were still present, (samples 02/03) individual "fat globules", like thick beads. With further metering, the "catalyst beads" settled out. Two phases remained, but TFA and amine diffused into the ester phase.
Result:

| Sample | % HCl | % EtOH | % TFAEt | % TFA | % Amine |
|---|---|---|---|---|---|
| 01 | 0.08 | 4.43 | 94.51 | | |
| 02 | 0.88 | 0.37 | 98.14 | | |
| 03 | 55.39 | | 37.51 | | |
| 04 | 0.73 | 0.19 | 86.17 | 7.49 | 5.39 |

Sample 04 was taken only after introduction 1:1, hydrolyzed. Samples 01, 02 and 04 were taken from the liquid ester phase, and Sample 03 from the gas phase above the reaction mixture.

EXAMPLE 4

| Batch: | 1.0 mole ethanol | 32.05 g |
|---|---|---|
| | 0.1 mole trifluoroacetic acid (TFA) | 11.40 g |
| | 0.1 mole N-methylpiperidine | 9.92 g |
| | 1.0 mole trifluoroacetyl chloride (TFAC) | 132.47 g |
| | 0.025 mole water | 0.45 g |

Set-up and Procedure:

The alcohol was introduced into a 250 ml three-necked flask, and the amine was weighed in. Then the trifluoroacetic acid was added dropwise very carefully. Then the water was also added, in order to produce a two-phase system. N-methylpiperidine did not react so vigorously with the TFA as e.g. DBN. The flask was provided with a dry-ice cooler (−70° C.) and heated to approximately 55° C. in an oil bath. At this temperature, TFAC was introduced with stirring. When approximately 30 g TFAC (~23 mole %) had been introduced, the solution became cloudy, and formed a clear, second phase (supernatant catalyst phase). Samples 01/02 were then taken. Sample 01 was analyzed once again after about 1 hour, since the catalyst phase had not yet completely separated. This sample was sample 03. When 89 g of TFAC (~67 mole %) had been added, two phases still existed. This sample was analysed as Sample 04. Phase combination occurred at approximately 72 mole % TFAC.

Result:

| Sample | % HCl | % EtCl | % EtOH | % TFAEt | % TFA | % Amine |
|--------|-------|--------|--------|---------|-------|---------|
| 01 | 1.60 |        | 10.01  | 81.58   | 1.95  | 4.46    |
| 02 | 40.36| 0,487  | 0.44   | 42.85   |       |         |
| 03 | 0.73 |        | 6.29   | 91.15   | 1.12  | 0.66    |
| 04 | 4.29 |        | 0.78   | 78.22   | 7.49  | 8.24    |

Samples 01 and 03 were taken from the liquid ester phase; sample 02 from the gas phase above the reaction mixture, and sample 04 after combination of he phases at the end of the reaction.

EXAMPLE 5

Use of DBU

| Batch: | 1.0 mole ethanol | 32.05 g |
|--------|------------------|---------|
|        | 0.2 mole trifluoroacetic acid (TFA) | 22.80 g |
|        | 0.1 mole 1,8-diazabicyclo[5.4.0]-undec-7-ene (DBU) | 15.20 g |
|        | 0.5 mole trifluoroacetyl chloride (TFAC) | 66.2 g |
|        | 0.1 mole water | 1.8 g |

Set-up and Procedure:

The alcohol was introduced into a 250 ml three-necked flask, and the amine was weighed in. Then the trifluoroacetic acid was added dropwise very carefully. DBU reacted very much more vigorously with the TFA than e.g. pyridine. The flask was provided with a reflux condenser (−40° C.) and heated to approximately 55° C. in an oil bath. At this temperature, the TFAC was introduced with stirring. When approximately 13 g TFAC (~10 mole %) had been introduced, the solution became cloudy, and thick yellow flakes precipitated. Sample 01 was taken. When 88 g (~68 mole %) had been added, only one phase was still present. After addition of one further equivalent of TFA, the precipitate dissolved. Sample 02 was then taken. Upon further introduction of TFAC, the precipitate formed again. Thereupon another 0,1 mole water was added, and after being left to stand for one hour, Sample 03 was taken from the resulting ester phase.

Result:

| Sample | % HCl | % EtCl | % EtOH | % TFAEt | % TFA |
|--------|-------|--------|--------|---------|-------|
| 01     | 0.91  |        | 4.63   | 91.55   | 2.08  |
| 02     | 49.86 | 1.51   | 0.09   | 44.67   |       |
| 03     | 0.34  |        | 0.41   | 98.76   |       |

Samples 01 and 03 were taken from the liquid ester phase, and Sample 02 was taken from the gas phase above the reaction mixture.

EXAMPLE 6

Use of an Excess of Trifluoroacetic Acid

| Batch: | 1.0 mole ethanol | 32.05 g |
|--------|------------------|---------|
|        | 0.25 mole trifluoroacetic acid | 28.50 g |
|        | 0.1 mole piperidine | 8.50 g |
|        | 1.0 mole trifluoroacetyl chloride | 132.47 g |

Set-up and Procedure:

The alcohol was introduced into a 250 ml three-necked flask, and the amine was weighed in. Then the 0.1 mole trifluoroacetic acid was added dropwise very carefully. The flask was provided with a reflux condenser (40° C.), and TFAC was introduced at room temperature with stirring, so that a temperature of 30° C. was not exceeded. When approximately 13 g TFAC had been added, the solution became cloudy, and crystals were precipitated. After introduction of 23.4 g TFAC, the addition was topped because the flask contents had become solid, and an oil bath heated to a controlled temperature of 70° C. was placed beneath the flask. At this temperature, the remaining TFA (approx. 18 g) was added. The salt dissolved, but did not initially form a second phase. After introduction of 50% of the above amount of TFAC, the phase separation then took place. Sample 01 was then taken. After addition of approximately 80% of the TFAC, sample 02 was taken from the gas phase in front of the cooler; sample 04 was taken from the gas phase after the cooler, and sample 03 shows the composition of the ester phase at that time. After further introduction of TFAC, phase mixing took place, i.e. the two-phase system disappeared after introduction of approx. 85% of the quantity of TFAC. After phase mixing, sample 05 was taken (hydrolyzed).

Result:

| Sample | % HCl | % TFAC | % EtCl | % EtOH | % TFAEt | % TFA |
|--------|-------|--------|--------|--------|---------|-------|
| 01     |       |        | 0.03   | 0.41   | 99.33   |       |
| 02     | 58.90 | 7.3    | 0.16   |        | 31.53   | 1.52  |
| 03     | 5.40  |        | 0.018  | 0.22   | 87.17   | 6.33  |
| 04     | 97.53 |        | 0.10   |        | 1.75    |       |
| 05     |       |        | 0.02   | 0.073  | 99.59   |       |

Samples 01 and 03 were taken from the liquid ester phase; sample 02 was taken from the gas phase above the reaction mixture, and sample 04 was taken following the cooler which was placed on top.

EXAMPLE 7

Preparation of Eethyl Trifluoroacetate (TFAEt) with DBN×3 TFA

Reaction Equation: $C_2H_5OH + CF_3COCl \rightarrow CF_3CO_2Et + HCl$

| Batch: | 1.0 mole ethanol | 46.07 g |
|---|---|---|
| | 0.3 mole trifluoroacetic acid (TFA) | 34.20 g |
| | 0.1 mole DBN | 12.40 g |
| | 1.0 mole trifluoroacetyl chloride (TFAC) | 132.47 g |

Set-up and Procedure

The alcohol and the amine were weighed into a 250 ml three-necked flask. Then the TFA was added dropwise very carefully. The DBN reacted very vigorously with the TFA. The flask was provided with a dry-ice cooler and heated to approximately 50° C. in an oil bath. Once this temperature was reached, TFAC was introduced with vigorous stirring. When approximately 40 g TFAC (≈30 mole %) had been introduced, the solution became cloudy. When 42 g of TFAC had been added, a second, clear phase formed (supernatant catalyst phase). When 125 g (≈94 g mole %) TFAC had been added, only one phase was still present (yellowish, clear). In the two-phase range, the purity of the TFAEt in the organic phase was already 98% without further purification. The conversion to TFAEt was complete. This example proves that the reaction also works using the adduct of DBN and trifluoroacetic acid with additional free acid.

EXAMPLE 8

Preparation of Methyl Chloride-free Methyl Trifluoroacetate (TFAMe) with DBN×3 TFA Reaction equation: $CH_3OH + CF_3COCl \rightarrow CF_3CO_2CH_3 + HCl$

| Batch: | 1.0 mole methanol | 32.04 g |
|---|---|---|
| | 0.3 mole trifluoroacetic acid | 34.20 g |
| | 0.1 mole DBN | 12.40 g |
| | 1.0 mole TFAC | 132.47 g |

Set-up and Procedure:

The alcohol and the amine were weighed into a 250 ml three-necked flask. Then the TFA was added dropwise very carefully. The DBN reacted very vigorously with the TFA. The flask was provided with a dry-ice cooler and heated to approximately 50° C. in an oil bath. Once this temperature was reached, TFAC was introduced with vigorous stirring. When approximately 26 g TFAC (≈20 mole %) had been introduced, the solution became cloudy. When 28 g TFAC had been added, a second, clear phase formed (supernatant catalyst phase). When 121 g TFAC (≈92 g mole %) had been added, only one phase was still present (yellowish, clear). In the two phase range, the purity of the TFAMe in the organic phase was already 99% without further purification. The conversion to TFAMe was complete. This example proves that methyl chloride-free product is obtained even when using the adduct of DBN and trifluoroacetic acid with additional free acid.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A process for preparing a carboxylic acid ester from an alcohol and a carboxylic acid, carboxylic acid chloride or carboxylic acid bromide, wherein esterification is effected while avoiding precipitation of "onium" salts, by operating in the presence of an onium salt adduct of the corresponding carboxylic acid and 1,5-diazabicyclo[4.3.0]-non-2-ene or 1,8-diazabicyclo[5.4.0]-undec-7-ene, or operating in the presence of the corresponding carboxylic acid and an onium salt of the corresponding carboxylic acid.

2. A process according to claim 1, wherein esterification is effected in the presence of two liquid phases.

3. A process according to claim 1, wherein a carboxylic acid ester corresponding to formula (I) or (II)

$$R^1-C(O)-OR^2 \qquad (I)$$

$$R^1-C(O)-CH_2-C(O)-OR^2 \qquad (II)$$

is prepared, wherein $R^1$ is aryl, C1–C4 alkyl or C1–C4 alkyl substituted by at least one halogen atom, and $R^2$ is C1–C4 alkyl, C1–C4 alkyl substituted by at least one halogen atom, aryl or benzyl.

4. A process according to claim 3, wherein $R^1$ is methyl, ethyl, or methyl or ethyl substituted by at least one halogen atom.

5. A process according to claim 1, wherein a caroxylic acid chloride is used as a starting material for the esterification.

6. A process according to claim 5, wherein the carboxylic acid ester is an alkyl ester of a halogenated acetic acid or halogenated acetylacetic acid, and wherein the acid chloride and an alkyl alcohol are esterified in the presence of an onium salt adduct of the corresponding halogenated acetic acid or halogenated acetylacetic acid and 1,5-diazabicyclo[4.3.0]-non-2-ene or 1,8-diazabicyclo[5.4.0]-undec-7-ene, or the corresponding halogenated acetic acid or halogenated acetylacetic acid and an onium salt of the corresponding halogenated acetic acid or halogenated acetylacetic acid.

7. A process according to claim 6, wherein the halogenated acetic acid or halogenated acetylacetic acid is produced in situ by addition of water to the reaction mixture.

8. A process according to claim 6, wherein the carboxylic acid ester is an alkyl ester of trifluoroacetic acid, difluoroacetic acid, chlorodifluoroacetic acid or trifluoroacetylacetic acid.

9. A process according to claim 1, wherein the onium salt and acid are present in a molar ratio in the range from 1:0.2 to 1:3.

10. A process according to claim 1, wherein a non-aromatic "onium" salts is used, whereby formation of alkyl chloride by-product is decreased.

11. A process according to claim 1, wherein an onium salt of a trialkylamine is used.

12. A process according to claim 1, wherein an onium salt of piperidine, N-alkylpiperidine, hydroxypiperidine or N-alkylhydroxy-piperidine is used.

13. A process according to claim 1, wherein the alcohol is a C1–C4 alkyl alcohol.

14. A process according to claim 13, wherein the alcohol is methyl alcohol or ethyl alcohol.

15. An "onium" salt formed from a carboxylic acid and a monocyclic or bicyclic amine compound with at least two nitrogen atoms, wherein at least one nitrogen atom is incorporated in the ring system.

16. A composition of matter comprising a mixture comprising a carboxylic acid and an "onium" salt of said carboxylic acid.

* * * * *